(12) United States Patent
Thiem et al.

(10) Patent No.: US 6,635,225 B1
(45) Date of Patent: Oct. 21, 2003

(54) AUTOMATIC STAINER FOR STAINING OBJECTS FOR MICROSCOPIC EXAMINATION

(75) Inventors: Stefan Thiem, Heidelberg (DE); Ralf Kaltenmeier, Nussloch (DE); Eric Barth, Leimen (DE); Joachim Glasenapp, Heddesheim (DE); Stefan Kunkel, Karlsruhe (DE)

(73) Assignee: Leica Microsystem Nussloch GmbH, Nussloch (DE)

( * ) Notice: Subject to any disclaimer, the term of this patent is extended or adjusted under 35 U.S.C. 154(b) by 0 days.

(21) Appl. No.: 09/542,873

(22) Filed: Apr. 4, 2000

(30) Foreign Application Priority Data

Apr. 23, 1999 (DE) .......................................... 199 18 442

(51) Int. Cl.[7] .............................. G01N 35/04; B05C 3/02
(52) U.S. Cl. ............................. 422/65; 422/63; 422/64; 422/102; 422/104; 436/43; 436/46; 436/47; 436/48; 427/2.11; 118/423; 118/425; 118/419
(58) Field of Search ................................ 422/63, 64–65, 422/104, 102; 436/43, 46–48; 427/2.11; 118/423, 425, 419

(56) References Cited

U.S. PATENT DOCUMENTS

| 3,837,795 | A | * | 9/1974 | Becker et al. | ............... | 118/423 |
|---|---|---|---|---|---|---|
| 3,976,028 | A | * | 8/1976 | Howells et al. | ............... | 118/421 |
| 4,436,764 | A | * | 3/1984 | Nakazima et al. | ........... | 118/423 |
| 4,738,824 | A | * | 4/1988 | Takeuchi | ..................... | 118/425 |
| 4,911,098 | A | | 3/1990 | Tabata | .......................... | 118/423 |
| 5,573,727 | A | | 11/1996 | Keefe | ........................... | 422/63 |
| 5,588,202 | A | * | 12/1996 | Ehlers et al. | ............... | 174/52.2 |
| 5,601,650 | A | | 2/1997 | Goldbecker et al. | ......... | 118/697 |
| 5,895,628 | A | | 4/1999 | Heid et al. | ...................... | 422/65 |
| 6,017,495 | A | * | 1/2000 | Ljungmann | .................. | 118/423 |
| 6,058,788 | A | * | 5/2000 | Thiem et al. | ................ | 422/101 |
| 6,080,363 | A | * | 6/2000 | Takahashi et al. | ........... | 118/625 |

FOREIGN PATENT DOCUMENTS

| DE | 41 17 830 | 12/1992 |
|---|---|---|
| DE | 41 17 831 | 12/1992 |
| DE | 41 17 833 | 10/1993 |
| DE | 196 52 339 | 6/1998 |

OTHER PUBLICATIONS

"COT 20 Tissue Stainer, Kontinuier . . . fur die Histologie und Sytologie ," http://www.medite–histotechnic.com/COT20DE.HTM (Non–English—10 pgs), date unknown.
Sakura Tissue–Tek® SCA™ Coverslipper Linear Stainer ll, date unknown.

* cited by examiner

Primary Examiner—Jill Warden
Assistant Examiner—P. Kathryn Bex
(74) Attorney, Agent, or Firm—Foley & Lardner

(57) ABSTRACT

An automatic stainer for staining objects, arranged on slides for microscopic examination is described. The automatic stainer has multiple reagent containers arranged one behind another for treating the objects. The slides pass through the reagent containers in succession, a transport basket for receiving multiple slides being provided. Multiple transport baskets can be received simultaneously in respective different reagent containers, and are simultaneously lifted out of the respective reagent container by way of a motorized transport mechanism having a lifting device and are respectively transported on into an adjacent reagent container. A removal station that has a collecting reagent container for the simultaneous reception of multiple transport baskets is arranged at the end of the row of reagent containers.

17 Claims, 3 Drawing Sheets

AUTOMATIC STAINER FOR STAINING OBJECTS FOR MICROSCOPIC EXAMINATION

CROSS REFERENCE TO RELATED APPLICATIONS

Reference is made to the German Patent Application 199 18 442.9-52 from which the present application claims priority.

FIELD OF THE INVENTION

This invention relates to an automatic stainer for staining objects, arranged on slides, for microscopic examination, in which multiple reagent containers arranged one behind another are provided for treating the objects, and the objects pass through the reagent containers in succession, having a transport basket for receiving multiple slides, such that multiple transport baskets can be received simultaneously in respective different reagent containers and the transport baskets are simultaneously lifted out of the respective reagent container by way of a motorized transport mechanism having a lifting device, and are transported on, one step in each case, into an adjacent reagent container.

BACKGROUND OF THE INVENTION

After being cut on a microtome, the histological objects provided for microscopic examination are placed onto slides. The slides are then correspondingly labeled and catalogued. To increase the contrast for a subsequent microscopic examination, these objects are stained, making the structures in the cells or the tissue visible in differentiated fashion. In addition to various special stains, a standard staining process has proven successful in practice. With this H. E. stain, the specimens pass through various processing steps with xylene, alcohol, eosin, hematoxylin, acetic acid, and water. Various types of automatic stainers, which convey the specimens automatically to the respective processing steps, are used to stain the objects. The automatic stainers differ in terms of their mechanical construction and their manner of operation.

DE 36 34 976 C2 discloses an automatic stainer having a plurality of reagent containers, arranged next to and behind one another, in which the slides are arranged in preparation holders and are transported by a transport apparatus to the various containers. With this stainer, different staining programs can be performed simultaneously. For that purpose, the preparation holder can be introduced individually via the transport apparatus, using a gripping and positioning apparatus configured as a "gantry crane," into any desired container, where it is uncoupled from the transport apparatus. With this transport apparatus, only a single preparation holder can be moved at one time. This results in only a low throughput of objects.

A further automatic stainer of two-row configuration, having reagent containers arranged one behind another, is known from DE 41 17 831 C2. Here as well, the preparation holders are transported individually to the various containers where they are uncoupled again from the transport apparatus. Here as well, multiple staining processes can be performed individually at the same time, but also with the disadvantage that only a relatively low throughput is possible.

An automatic stainer for the H.E. staining method with elevated throughput is described in U.S. Pat. No. 4,911,098. The stainer has multiple reagent containers arranged one behind another, into which the objects, arranged in preparation holders, are introduced via a transporting and gripping apparatus. After introduction, here as well the preparation holders are uncoupled from the gripping apparatus. An elevated throughput is achieved by the fact that multiple transporting and gripper apparatuses can be present simultaneously in the automatic stainer. The arrangement of multiple transporting and gripping apparatuses is of course associated with a very high level of complexity.

Further automatic stainers having a simplified transport mechanism and a high preparation throughput are offered by the company styled "medite" under the name "COT 20," and by the company styled "Sakura" under the name "Linear Slide Stainer II." Both automatic stainers operate on the principle of a continuously returning transport movement for the transport baskets in which the slides with the objects are located. In the course of the transport movement, the transport baskets are transported at constant cycling rates into the reagent containers arranged one behind another. A requisite residence time for the objects in the respective containers is achieved by way of multiple reagent containers arranged one behind another. The transport basket is suspended in a transport bar, and conveyed a specific distance by the transport bar to the next reagent container where it is lowered again. The transport bar travels back, under the supporting clip of the transport basket, into its initial position. A further transport basket can now be placed on the transport bar. Once a predefined cycle time has elapsed, the transport bar simultaneously lifts up all the transport baskets present in the automatic stainer and transports them into the next reagent container. At the last reagent container, a sensor is provided that is triggered by the transport basket and triggers a corresponding signal. The process is then continued until the corresponding transport basket is removed. It is disadvantageous in this case that the automatic stainer must be continuously monitored, since otherwise the specimens remain too long in the respective reagent containers and become unusable.

In practice, these automatic stainers are discontinuously loaded, so that gaps or unused cycle times exist between the individual transport baskets or a group thereof. The operator must therefore continuously ensure that the transport baskets are removed at the correct time.

SUMMARY OF THE INVENTION

It is therefore the object of the present invention to create a greater flexibility in the monitoring of an automatic stainer of this kind, and at the same time to simplify the removal of transport baskets.

According to the present invention, this object is achieved by the features recited in the characterizing portion of claim 1. Further advantageous developments are the subject matter of the dependent claims.

The automatic stainer is characterized in that a removal station having a collecting reagent container for the stained objects is arranged at the end of the row of reagent containers. This collecting reagent container is configured such that multiple transport baskets can be received simultaneously. The temporal sequence in which the transport baskets arrive in the collecting container is also immaterial in this context. Even long time intervals or cycle times between the individual incoming transport baskets are possible, with no need for intervention by an operator. Transport is interrupted only when the collecting container is completely filled with transport baskets. In addition, this collecting container is preferably filled with xylene or another corresponding liquid. Objects that have already been processed are thereby prevented from drying out and becoming unusable for subsequent microscopic examination.

In an embodiment of the invention, provision is made for the lifting device to be equipped, in the region of the collecting reagent container, with a stepped profile. The result of this is that the transport baskets are lifted up only slightly, and are transported on in steps into the collecting reagent container until an end stop limits further transport. The drive system is not stopped at this time. This is made possible by the stepped profile on the slide bar. The transport basket is merely lifted a short distance by the lifting device, and transported on. If the transport basket encounters, in this context, an end stop or another transport basket, the slide bar merely slides along on the transport basket. This ensures that the transport baskets become lined up one behind another in the collecting reagent container.

In a further embodiment of the invention, provision is made for the removal station to have a sensor arranged opposite the end stop. This sensor becomes active only when the collecting reagent container is completely filled with transport baskets.

The removal station has at least one ramp over which the transport baskets slide into the collecting reagent container and by way of which the sensor can be triggered. For that purpose, a spring-loaded lever is associated with the ramp. When a transport basket is delivered onto the ramp, the lever is moved and triggers the sensor. At the same time, the transport basket slides on the ramp completely into the collecting reagent container. This cancels the sensor signal again. Only when the collecting container is completely filled with transport baskets is it impossible for any further baskets to slide over the ramp, and the sensor remains activated.

In a further embodiment of the invention, the control circuit connected to the sensor is equipped with a time-delay logic system. This logic system ensures that corresponding optical and/or acoustic signals and/or signals for the transport mechanism are emitted only if the sensor signal is present uninterruptedly for a certain time.

In an advantageous embodiment, the sensor is configured as a completely encapsulated proximity sensor, so that no aggressive liquids or vapors can penetrate into the sensor and damage it.

Advantageously, the removal station is configured as a separate and retrofittable module.

BRIEF DESCRIPTION OF THE DRAWINGS

The invention will be explained in further detail with reference to an exemplary embodiment with the aid of the schematic drawings, in which.

DETAILED DESCRIPTION OF THE INVENTION

Figure 1:
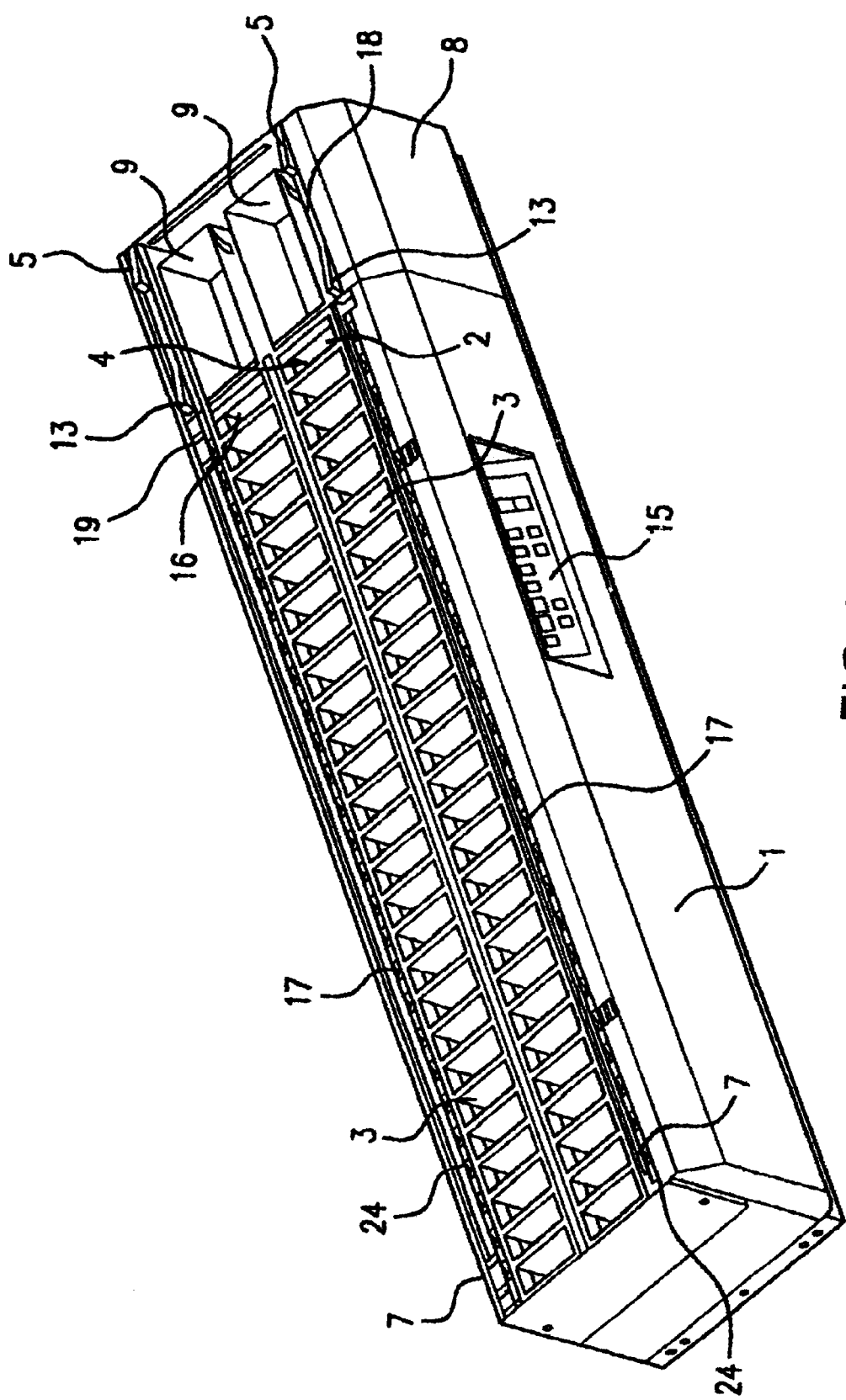
FIG. 1 shows a view of the automatic stainer with the removal station in place.

FIG. 1 shows an automatic stainer 1 having a control panel 15 and having two rows of multiple reagent containers 3 arranged one behind another. A removal station 8, having one collecting reagent container 9 for each reagent container row, is arranged at the right-hand end of automatic stainer 1.

A transport basket 4 having multiple slides 2 is hooked into one of reagent containers 3 via a transport clip 16. Motorized transport mechanism 6 has a lifting device 7 with which transport baskets 4 are moved in steps from left to right. Lifting device 7 has a transport arm 24 arranged respectively on the right-hand and left-hand row of reagent containers. The two arms 24 are immovably joined to one another. Lifting device 7 is equipped with transport notches 17 into which transport clips 16 are placed while moving.

During the transport movement, baskets 4 are transported into reagent containers 3 arranged one behind another. For that purpose, transport basket 4 is hooked into the first notch 17 of lifting device 7. Lifting device 7 lifts transport basket 4 completely out of reagent container 3, waits for a specific dripping time, moves transport basket 4 horizontally to the next reagent container 3, and there lowers transport basket 4 down again. In this context, lifting device 7 is lowered until transport clips 16 release from transport notches 17 and are supported on the frame of reagent container 3 or on the frame of automatic stainer 1. Lifting device 7 is now free, and travels back into its initial position under transport clip 16 of transport basket 4. Once a predefined cycle time has elapsed, lifting device 7 simultaneously lifts up all transport baskets 4 and transports them into the next reagent container 3. Provided on the last reagent container 3 is a sensor 19 that is triggered by transport basket 4 and triggers a corresponding signal. When the removal station is fitted, this sensor 19 is deactivated.

From the last reagent container 3, transport basket 4 is conveyed by lifting device 7 into removal station 8, and initially deposited with transport clip 16 onto a ramp 13 that is attached on a retaining bar 18. From there, transport basket 4 slides completely into collecting reagent container 9, supporting itself with transport clip 16 on retaining bar 18. An end stop 5 is attached on retaining bar 18 opposite ramp 13.

Figure 2:
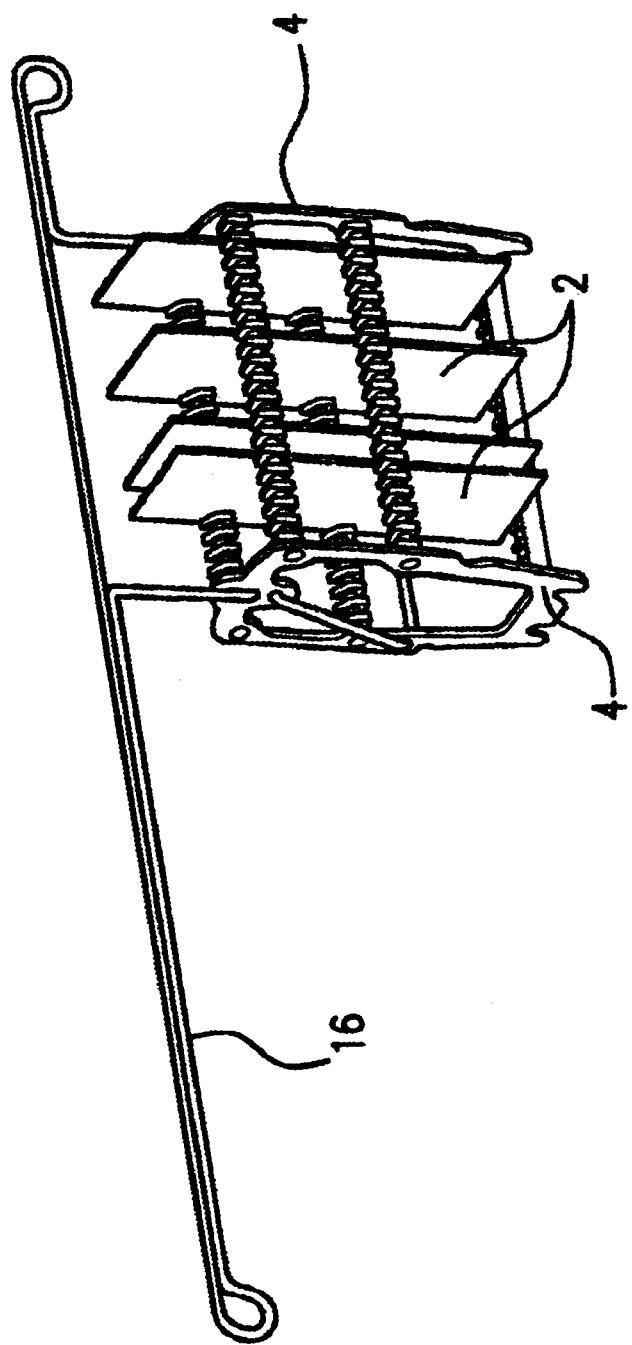
FIG. 2 shows a view of a transport basket with slides.

FIG. 2 shows a transport basket 4 having four slides 2 placed in it. A transport clip 16 is detachably attached to transport basket 4.

Figure 3:
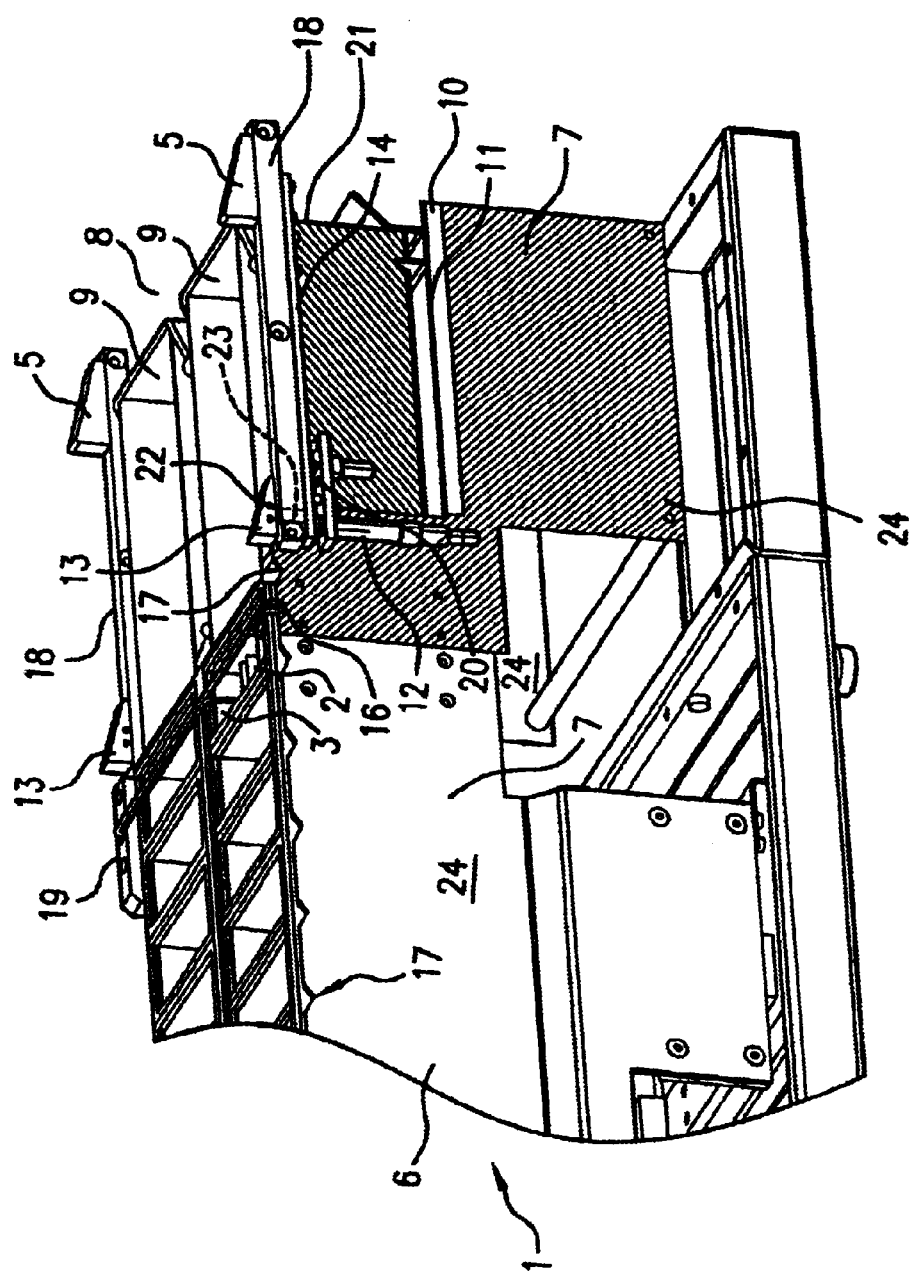
FIG. 3 shows a view of the removal station arranged on the automatic stainer.

FIG. 3 shows a view of removal station 8, with lifting device 7 and transport notches 17, arranged on automatic stainer 1. In the region of removal station 8, the lifting device has only one transport notch 17. Adjacent thereto, lifting device 7 is equipped with a stepped profile 10 located lower down, so that in the course of the lifting movement, transport clip 16 located on retaining bar 18 is lifted up only a small amount. This amount corresponds to, at most, the height of end stop 5.

Stepped profile 10 is additionally equipped with a slide bar 11 over which transport clip 16 slides when transport basket 4 comes to a stop either against end stop 5 or against a further transport basket 4. Collecting reagent container 9 is thus continuously filled with incoming transport baskets 4. It is immaterial in this context if a transport basket 4 is deposited in collecting reagent container 9 with each transport cycle, or if one or more idle cycles elapse between baskets 4.

Collecting reagent container 9 can continue to receive transport baskets 4 until a basket 4 can no longer slide off ramp 13. For this situation, ramp 13 is equipped with a pin 22 that is guided through a hole 23 in retaining bar 18 and braces against a lever 14. Lever 14 is mounted on retaining bar 18 movably by way of a compression spring 20 and a retainer 21. Arranged below lever 14 is a sensor 12 that is electrically connected to a control circuit 25 (not depicted in FIG. 3). Sensor 12 is configured as a proximity sensor, and is triggered by lever 14 that is moved downward by ramp 13.

Sensor 12 of course responds each time a transport basket 4 and its transport clip 16 is deposited. To ensure that a corresponding warning signal is not triggered each time, the control circuit 25 is equipped with a time-delay logic system 26. Only after lifting device 7 has moved back to its initial position is the status of sensor 12 interrogated, and a corresponding sensor signal evaluated.

The invention has been described with reference to a specific embodiment but it is clear that a person skilled in the art may carry out amendments and modifications without departing from the scope of the claims below.

PARTS LIST

1 Automatic stainer
2 Slide
3 Reagent container
4 Transport basket
5 End stop
6 Transport mechanism
7 Lifting device
8 Removal station
9 Collecting reagent container
10 Stepped profile
11 Slide bar
12 Sensor
13 Ramp
14 Lever
15 Control panel
16 Transport clip
17 Transport notch
18 Retaining bar
19 Sensor on 1
20 Compression spring
21 Retainer of 14 on 18
22 Pin on 13
23 Hole in 18
24 Transport arm

What is claimed is:

1. An automatic stainer for staining objects on slides for microscopic examination, comprising:
   (a) multiple reagent containers arranged in a row for treating the objects on slides, wherein the slides pass through the reagent containers in succession and wherein the multiple reagent containers comprise a last container, the last container being a collecting reagent container;
   (b) multiple transport baskets for receiving said slides wherein more than one transport basket is received simultaneously in respective different reagent containers;
   (c) transport clips detachably attached to the transport baskets;
   (d) a motorized transport mechanism comprising a lifting device for simultaneously lifting out said transport baskets of the respective reagent container with the transport clips and transporting said transport baskets, one step in each case, into an adjacent reagent container;
      (i) the lifting device comprising a transport arm with a step profile;
      (ii) the transport arm, in the region of the reagent containers, comprises a first transport arm section which comprises a transport notch for the receipt of the transport clips during transport;
      (iii) the transport arm, in the region of the collecting reagent container, comprises a slide bar for the receipt of the transport clips during transport of the transport baskets in the collecting reagent container; and
      (iv) the slide bar of the transport arm is arranged below the transport notch; and
   (e) a removal station comprising the collecting reagent container for receiving of said multiple transport baskets arranged at the end of said row of reagent containers; and
   wherein said stepped profile is in the region of the collecting reagent container, so that the transport baskets are lifted up into the collecting reagent container and then are transported on in steps within said collecting reagent container and wherein the step profile of the transport arm is made from the transport arm section and the slide bar.

2. The automatic stainer as defined in claims 1, wherein at least one end stop is provided on said removal station for a transport basket.

3. The automatic stainer as defined in claim 2, wherein a sensor is arranged opposite to the end stop of the removal station.

4. The automatic stainer as defined by claim 3, wherein at least one ramp is provided at the removal station for triggering the sensor.

5. The automatic stainer as defined in claim 3, wherein the sensor is connected to a control circuit which emits a control signal.

6. The automatic stainer as defined in claim 5, wherein said control signal is an optical signal.

7. The automatic stainer as defined in claim 5, wherein said control signal is an acoustic signal.

8. The automatic stainer as defined by claim 5, wherein said control signal is a signal for controlling the transport mechanism.

9. The automatic stainer as defined in claim 5 wherein said control signal is an optical signal and a signal for the transport mechanism.

10. The automatic stainer as defined by claim 5 wherein said control signal is an optical signal and a signal for controlling the transport mechanism.

11. The automatic stainer as defined by claim 5 wherein said control signal is an acoustic signal and a signal for controlling the transport mechanism.

12. The automatic stainer as defined by claim 5, wherein said control signal is an optical signal, an acoustic signal and a signal for controlling the transport mechanism.

13. The automatic stainer (1) as defined in claim 5, wherein a time-delay logic system is associated with the control circuit.

14. The automatic stainer as defined in claim 3, wherein the sensor is configured as an encapsulated proximity sensor.

15. The automatic stainer as defined in claim 4, wherein a spring-loaded lever for triggering the sensor is associated with said ramp.

16. The automatic stainer as defined in claim 1, wherein the removal station is configured as a retrofittable separate module.

17. An automatic stainer for staining objects on slides for microscopic examination, comprising:
   (a) multiple reagent containers arranged in a row for treating the objects on slides, wherein the slides pass through the reagent containers in succession and wherein the multiple reagent containers comprise a last container, the last container being a collecting reagent container;

(b) multiple transport baskets for receiving said slides wherein more than one transport basket is received simultaneously in respective different reagent containers;

(c) transport clips detachably attached to the transport baskets;

(d) a motorized transport mechanism comprising a lifting device for simultaneously lifting out said transport baskets of the respective reagent container with the transport clips and for transporting said transport baskets, one step in each case, into an adjacent reagent container;
  (i) the lifting device comprising a transport arm with a step profile;
  (ii) the transport arm, in the region of the reagent containers, comprises a first transport arm section which comprises a transport notch for the receipt of the transport clips during transport;
  (iii) the transport arm, in the region of the collecting reagent container, comprises a slide bar for the receipt of the transport clips during transport of the transport baskets in the collecting reagent container; and
  (iv) the slide bar of the transport arm is arranged below the transport notch; and (e) a removal station comprising the collecting reagent container for the simultaneously receiving of said multiple transport baskets arranged at the end of said row of reagent containers and wherein the step profile of the transport arms is made from the first transport arm section and the slide bar;

wherein said stepped profile is in the region of the collecting reagent container, so that the transport baskets are lifted up into the collecting reagent container and then are transported in steps within the collecting reagent container, (g) a sensor arranged opposite an end stop of the removal station;

(f) a control circuit connected to the sensor; and (h) a time-delay logic system associated with the control circuit.

\* \* \* \* \*